(12) United States Patent  
Schumacher

(10) Patent No.: US 6,926,004 B2  
(45) Date of Patent: Aug. 9, 2005

(54) BREATHING MASK WITH A HEAD FASTENING DEVICE

(75) Inventor: Gerhard Schumacher, Bunde (DE)

(73) Assignee: Weinmann Geräte für Medizin GmbH & Co. KG, Hamburg (DE)

( * ) Notice: Subject to any disclaimer, the term of this patent is extended or adjusted under 35 U.S.C. 154(b) by 0 days.

(21) Appl. No.: 10/921,767

(22) Filed: Aug. 19, 2004

(65) Prior Publication Data

US 2005/0039753 A1    Feb. 24, 2005

(30) Foreign Application Priority Data

Aug. 20, 2003    (DE) ................ 103 38 169

(51) Int. Cl.[7] ............................................ A62B 18/08
(52) U.S. Cl. ...................... 128/206.27; 128/206.21; 128/201.22; 128/201.23; 128/201.24; 128/201.29; 128/203.29; 128/205.25; 128/206.12; 128/206.24; 128/206.28; 128/207.11; 128/207.17
(58) Field of Search ...................... 128/206.27, 206.21, 128/200.24, 201.22, 201.23, 201.24, 201.29, 128/203.29, 205.25, 206.12, 206.24, 206.28, 128/207.11, 207.17

(56) References Cited

U.S. PATENT DOCUMENTS

| 2,348,074 | A | * | 5/1944 | Lambertsen | ............ | 128/205.17 |
| 2,402,984 | A | * | 7/1946 | Browne | ................ | 128/205.13 |
| 2,827,900 | A | * | 3/1958 | Marietta | ................ | 128/206.28 |
| 6,044,844 | A | * | 4/2000 | Kwok et al. | ............ | 128/207.11 |
| 6,112,746 | A | * | 9/2000 | Kwok et al. | ............ | 128/207.13 |
| 6,119,693 | A | * | 9/2000 | Kwok et al. | ............ | 128/207.11 |
| 6,374,826 | B1 | * | 4/2002 | Gunaratnam et al. | .. | 128/206.27 |
| 6,435,181 | B1 | * | 8/2002 | Jones et al. | ............. | 128/204.18 |
| 6,467,483 | B1 | * | 10/2002 | Kopacko et al. | ....... | 128/207.12 |
| 6,494,207 | B1 | * | 12/2002 | Kwok | ................... | 128/207.11 |
| 6,532,961 | B1 | * | 3/2003 | Kwok et al. | ............ | 128/206.21 |
| 6,615,832 | B1 | * | 9/2003 | Chen | ..................... | 128/206.26 |
| 6,615,834 | B2 | * | 9/2003 | Gradon et al. | ......... | 128/207.11 |

FOREIGN PATENT DOCUMENTS

| DE | 141110 | 4/1980 |
| DE | 299 23 126 U1 | 5/2000 |
| DE | 696 09 341 T2 | 12/2000 |
| DE | 198 17 332 C2 | 11/2002 |
| DE | 102 54 399 A1 | 6/2004 |

* cited by examiner

*Primary Examiner*—Henry Bennett  
*Assistant Examiner*—Nihir Patel  
(74) *Attorney, Agent, or Firm*—Friedrich Kueffner

(57) ABSTRACT

A breathing mask is joined with a head fastening device that has at least one headstrap and at least one neckstrap. The headstrap and the neckstrap are connected with each other in the area of their extensions away from the breathing mask. The headstrap is fastened to the breathing mask at the top, and the neckstrap is fastened to the breathing mask at the sides in the orientation of the breathing mask when it is being worn. Regions of the neckstrap that are located next to the breathing mask are connected with one another by a chinstrap. The chinstrap extends essentially in the longitudinal direction of the neckstrap. End segments of the neckstrap, which are arranged between the breathing mask and the places at which the neckstrap is connected with the chinstrap, run towards the breathing mask at an angle of inclination relative to the chinstrap, so that they move farther and farther away from the chinstrap as they approach the breathing mask.

17 Claims, 3 Drawing Sheets

BREATHING MASK WITH A HEAD FASTENING DEVICE

BACKGROUND OF THE INVENTION

1. Field of the Invention

The invention relates to a breathing mask with a head fastening device, in which the head fastening device has at least one headstrap and at least one neckstrap, which are connected with each other in the area of their extensions away from the breathing mask. The headstrap is fastened to the breathing mask at the top, and the neckstrap is fastened to the breathing mask at the sides in the orientation of the breathing mask when it is being worn. The regions of the neckstrap that are located next to the breathing mask are connected with one another by a chinstrap.

2. Description of the Related Art

Various embodiments of head fastening devices of this type for breathing masks are already known. The neckstraps of previously known head masks are typically designed in such a way that, when they are worn, they run below the ears in the cheek region. Also well known are head fastening devices with additional lateral headstraps that run directly above the ears of the patient. The previously known head masks are functionally designed in such a way that they are optimized with respect to the fastening of the mask on the face of the patient. This standard design gives rise to angles of traction and tensile forces in the region of the neckstrap and the headstrap which tend to be randomly and for the most part nonuniformly distributed.

To prevent mouth breathing during respiration carried out with the use of a breathing mask, it is also already well known that a chinstrap can additionally be used to prevent involuntary opening of the mouth as the patient sleeps. The chinstrap is usually designed as a chin binder.

When the previously known head fastening devices are worn, the patient often finds it unpleasant that locally unpleasant forces are introduced in the head region by unfavorable angles of traction and the introduction of uneven forces, and that chafing occurs in places where the straps run close to the ears.

SUMMARY OF THE INVENTION

The object of the present invention is to provide a breathing mask with a head fastening device of the type described above in which functional fastening of the breathing mask on the patient's face is supported and a high degree of wearing comfort is achieved.

In accordance with the invention, this object is achieved by the fact that the chinstrap extends essentially in the longitudinal direction of the neckstrap, and that end segments of the neckstrap, which are arranged between the breathing mask and the places at which the neckstrap is connected with the chinstrap, run towards the breathing mask at an angle of inclination relative to the chinstrap, so that they move farther and farther away from the chinstrap as they approach the breathing mask.

The arrangement of the end segments of the neckstrap at an angle of inclination relative to the course of the chinstrap promotes a course of the neckstrap that both guarantees reliable fastening of the breathing mask on the patient's face and prevents the formation of chafing sites near the patient's ears. Furthermore, this also promotes a uniform distribution of the angles of traction and a uniform distribution of the tensile forces. The result is a uniformly designed head fastening device with chin binding.

As a result of the inclined arrangement of the end segments of the neckstrap, both forces directed vertically downward and forces directed to the rear with respect to the patient's head are introduced into the breathing mask. Since, at the same time, upwardly directed forces and forces directed to the rear with respect to the patient's head are introduced into the breathing mask through the headstrap, exactly defined positioning of the breathing mask on the face of the patient is promoted on all sides, and this positioning is maintained with a high degree of reliability even in the case of stresses introduced into the mask by movements of the patient or movements of the breathing hose.

Advantageous dimensioning, both to guarantee a high degree of fastening reliability for the breathing mask and to achieve a high degree of wearing comfort, is characterized by the fact that the angle of inclination between the chinstrap and at least one of the end segments has a value of 10–70°.

It was found to be especially advantageous for the angle of inclination to have a value of 20–45°.

It helps to achieve a compact design if the head fastening device has exactly one headstrap.

Locally distributed introduction of forces can be achieved if the head fastening device has exactly two headstraps.

In a typical area of application, the head fastening device is designed to support CPAP ventilation.

To further enhance wearing comfort, the headstrap can be made of a flexible material.

A neckstrap made of a flexible material also contributes to a high degree of wearing comfort.

To achieve an advantageous orientation of the angle of traction, it is helpful if the headstrap is approximately perpendicular to the neckstrap in the area in which it joins the neckstrap.

To help achieve simple manufacturing, it is proposed that the end segments be formed on the neckstrap as a single piece with the neckstrap.

A simple geometry of the individual components is achieved by manufacturing the end segments separately from the neckstrap and fastening them to the neckstrap.

To further enhance the wearing comfort, a forehead support is provided in the area of an upper fastening device connected with the base of the breathing mask.

Adaptation to the anatomy of different patients is facilitated by making it possible to vary the positioning of the forehead support in the area of the upper fastening device.

The distance between the breathing mask and the chinstrap can be set in advance by providing a length adjustment device in the area of at least one of the end segments.

Improved adjustment comfort can be achieved by providing at least one length adjustment device in the area of the neckstrap.

Length adjustment in the area of the neckstrap is made possible by providing at least one closure in the area of the neckstrap.

Use by both right-handed and left-handed individuals is facilitated if the neckstrap has two closures arranged on the sides and opposite each other.

The various features of novelty, which characterize the invention, are pointed out with particularity in the claims annexed to and forming part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
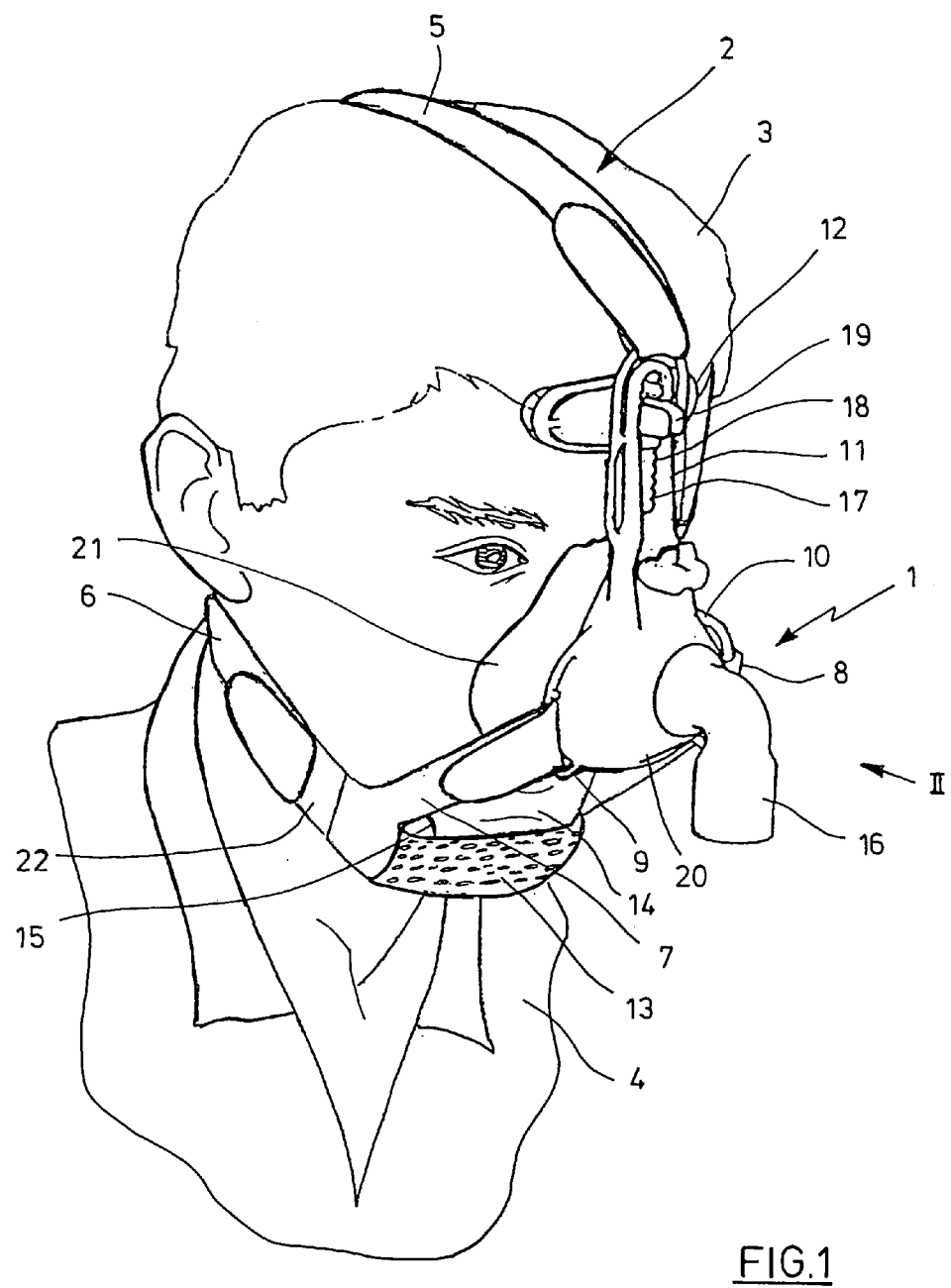
FIG. 1 is a perspective view of a breathing mask with a head fastening device as worn on a patient's head.

The drawing in FIG. 1 illustrates the arrangement of a breathing mask 1 with a head fastening device 2 on the head 3 of a patient 4. The head fastening device 2 has a headstrap 5 and a neckstrap 6. The neckstrap 6 is connected by end segments 7, 8 with lateral fastening devices 9, 10 of the breathing mask 1.

The headstrap 5 is connected with the head fastening device 2 by an upper fastening device 11. In addition, in the area of the upper fastening device 11, a forehead support 12 is supported in such a way that its position can be adjusted. The headstrap 5 and the neckstrap 6 are connected to each other in an area behind the head 3, which cannot be seen in the drawing.

In the areas of the transitions of the end segments 7, 8 into the remaining area of the neckstrap 6, a chinstrap 13 is attached, which, when the breathing mask is being worn, passes over the chin 14 of the patient 4. The end segments 7, 8 run in the direction of the breathing mask 1 at an angle of inclination 15, so that they become increasingly far from the chinstrap 13 as they approach the breathing mask 1.

A coupling element 16 for the attachment of a breathing hose is located in the area of the breathing mask 1. In particular, the coupling element 16 can be movably mounted in the area of the breathing mask 1. The mobility can be realized, for example, by a ball-and-socket joint. With respect to the ability to vary the positioning of the forehead support 12, it can be positioned along the forehead of the patient 4 both in the vertical direction and in the transverse direction. The ability to position the forehead support 12 can be realized, for example, by a slot 18 provided with catches 17 in the area of the upper fastening device 11, within which the forehead support 12 is clamped with a socket element 19. A flexible fabric, for example, can be used as the material for the headstrap 5 and the neckstrap 6. A soft fabric that is permeable to moisture is used as the material for the chinstrap 13. The breathing mask 1 has a base 20, which preferably consists of a mechanically stable plastic, and a contour element 21, which fits against the face of the patient 4 and consists of a very soft and pliable plastic.

Figure 2:
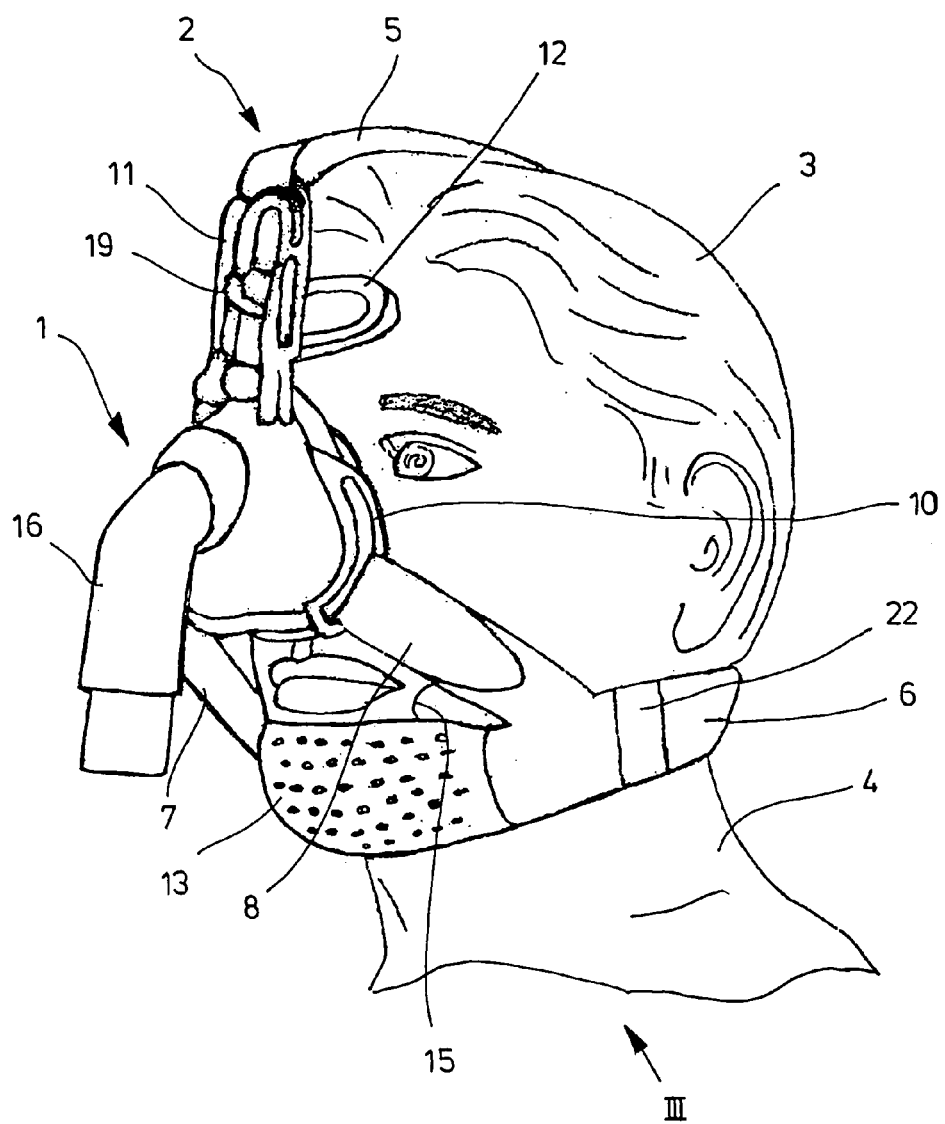
FIG. 2 is a view of the breathing mask with a head fastening device in the direction of arrow II in FIG. 1.

FIG. 2 illustrates the arrangement of the breathing mask 1 with the head fastening device in a different perspective view. In particular, the drawing again shows the arrangement of the angle of inclination 15 and the resulting inclined arrangement of the end segments 7, 8 relative to the chinstrap 13.

Figure 3:
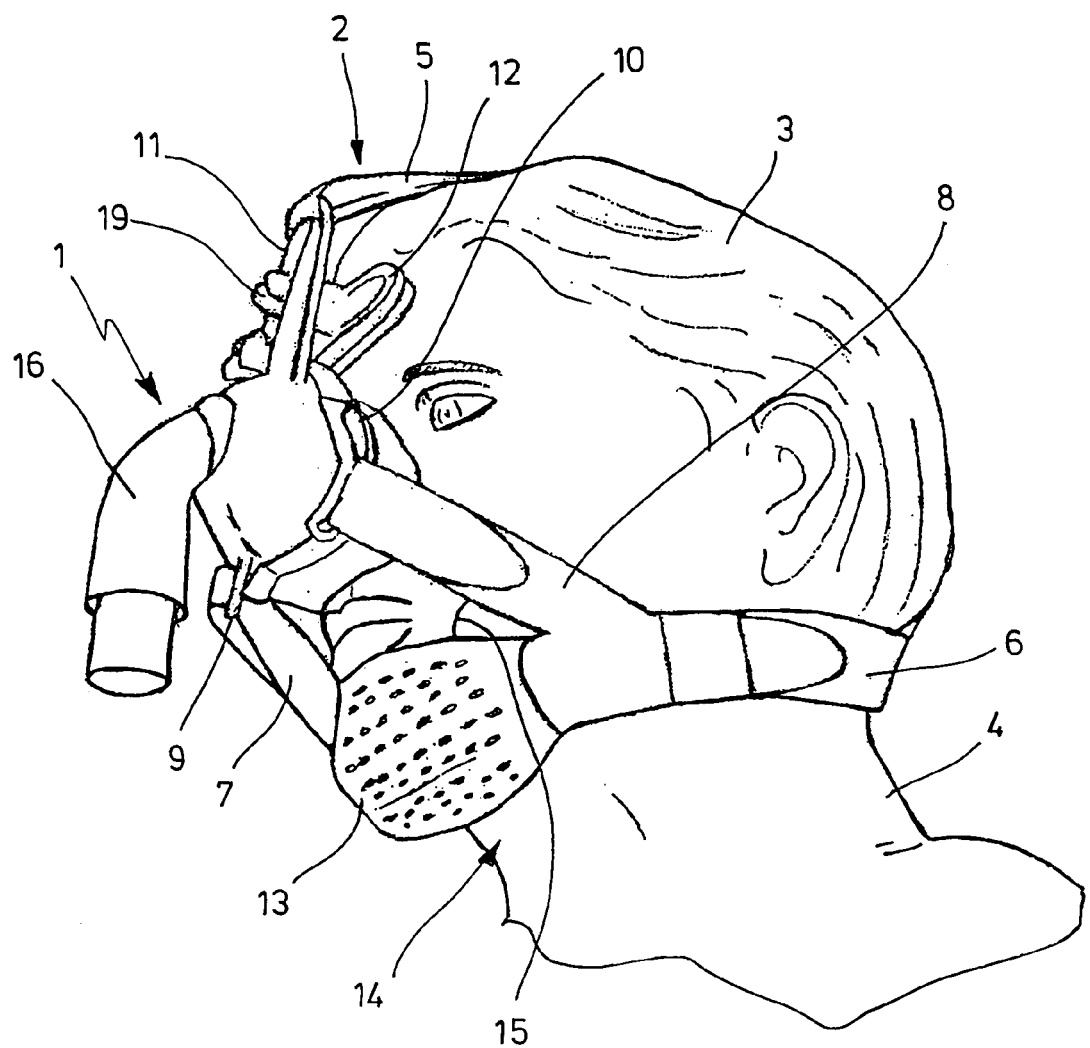
FIG. 3 is a view of the breathing mask with a head fastening device in the direction of arrow III in FIG. 2.

FIG. 3 shows that the chinstrap 13 extends over a large area around the chin 14 of the patient 4. In the area of the head of the patient 4, this supports good and uniform absorption of both the rearward-acting forces introduced by the neckstrap 6 and the upwardly directed forces introduced by the headstrap 5, the breathing mask 1, and the end segments 7, 8. At the same time, this immobilizes the chin 14 of the patient 4 to prevent involuntary opening of the mouth.

The drawings also specifically show that both the end segments 7, 8 and the neckstrap 6 are provided with length adjustment devices. In the illustrated embodiments, the length adjustment devices have a loop-like design, and the facing surfaces of the members can be provided with Velcro-like fasteners. For example, after the Velcro-like fasteners have been detached, the ends of the end segments 7, 8 can be suitably pushed through the lateral fastening devices 9, 10 to make the desired length adjustment. With respect to the neckstrap 6, it is possible either to provide only one length adjustment device or to realize a bilateral arrangement of two length adjustment devices to assist handling by both left-handed and right-handed individuals.

Moreover, in the illustrated embodiments, the neckstrap 6 is provided with two closures 22, which are designed as snap closures. Basically, the use of one closure is sufficient here also, but the use of two closures 22 assists handling by both left-handed and right-handed individuals in this case as well. The closures 22 make it possible to put the breathing mask 1 on and to take it off without having to make a length adjustment of the neckstrap 6. After the breathing mask 1 has been taken off and then put on again, the original length adjustments are thus still available unchanged.

The invention is not limited by the embodiments described above which are presented as examples only but can be modified in various ways within the scope of the protection defined by the appended patent claims.

I claim:

1. A breathing mask comprising a head fastening device, wherein the head fastening device has at least one headstrap and at least one neckstrap which are connected with each other in an area of their extensions away from the breathing mask; wherein, in the orientation of the breathing mask when it is being worn, the headstrap is fastened to the breathing mask at a top thereof and the neckstrap is fastened to the breathing mask at sides thereof; wherein regions of the neckstrap that are located next to the breathing mask are connected with one another by a chinstrap; wherein the chinstrap extends essentially in the longitudinal direction of the neckstrap; and wherein end segments of the neckstrap, which are arranged between the breathing mask and the places at which the neckstrap is connected with the chinstrap, extend towards the breathing mask at an angle of inclination relative to the chinstrap, so that they are located farther and farther away from the chinstrap as they approach the breathing mask.

2. The breathing mask in accordance with claim 1, wherein the angle of inclination between the chinstrap and at least one of the end segments has a value of 10–70°.

3. The breathing mask in accordance with claim 1, wherein the angle of inclination has a value of 20–45°.

4. The breathing mask in accordance with claim 1, wherein the head fastening device has exactly one headstrap.

5. The breathing mask in accordance with claim 1, wherein the head fastening device has exactly two headstraps.

6. The breathing mask in accordance with claim 1, wherein the head fastening device is adapted to support CPAP ventilation.

7. The breathing mask in accordance with claim 1, wherein the headstrap is of a flexible material.

8. The breathing mask in accordance with claim 1, wherein the neckstrap is of a flexible material.

9. The breathing mask in accordance with claim 1, wherein the headstrap is approximately perpendicular to the neckstrap in the area in which the headstrap joins the neckstrap.

10. The breathing mask in accordance with claim 1, wherein the end segments are formed on the neckstrap as a single piece with the neckstrap.

11. The breathing mask in accordance with claim 1, wherein the end segments are manufactured separately from the neckstrap and fastened to the neckstrap.

12. The breathing mask in accordance with claim 1, wherein a forehead support is provided in an area of an upper fastening device connected with the base of the breathing mask.

13. The breathing mask in accordance with claim 12, wherein the positioning of the forehead support can be varied in the area of the upper fastening device.

14. The breathing mask in accordance with claim 1, wherein a length adjustment device is provided in the area of at least one of the end segments.

15. The breathing mask in accordance with claim 1, wherein at least one length adjustment device is provided in the area of the neckstrap.

16. The breathing mask in accordance with claim 1, wherein at least one closure is provided in the area of the neckstrap.

17. The breathing mask in accordance with claim 16, wherein the neckstrap has two closures arranged on the sides and opposite each other.

* * * * *